US008558015B2

(12) United States Patent
Fisher et al.

(10) Patent No.: US 8,558,015 B2
(45) Date of Patent: Oct. 15, 2013

(54) SOLVENT ADDITION AND REMOVAL IN THE HYDROGENATION OF CATMINT OIL

(75) Inventors: John Charles Fisher, Kingston (CA); Keith W. Hutchenson, Lincoln University, PA (US); Scott Christopher Jackson, Wilmington, DE (US); Leo Ernest Manzer, Wilmington, DE (US); Mark A. Scialdone, West Grove, PA (US); Mayis Seapan, Landenberg, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 434 days.

(21) Appl. No.: 12/520,173

(22) PCT Filed: Dec. 20, 2007

(86) PCT No.: PCT/US2007/025984
§ 371 (c)(1),
(2), (4) Date: Jan. 18, 2010

(87) PCT Pub. No.: WO2008/079251
PCT Pub. Date: Jul. 3, 2008

(65) Prior Publication Data
US 2010/0145078 A1 Jun. 10, 2010

Related U.S. Application Data

(60) Provisional application No. 60/876,563, filed on Dec. 21, 2006, provisional application No. 60/876,565, filed on Dec. 21, 2006.

(51) Int. Cl.
*C07D 311/02* (2006.01)
(52) U.S. Cl.
USPC .......................................................... 549/283
(58) Field of Classification Search
USPC .......................................................... 549/283
See application file for complete search history.

(56) References Cited

U.S. PATENT DOCUMENTS

| | | | |
|---|---|---|---|
| 4,496,467 A | 1/1985 | Munteanu |
| 4,869,896 A | 9/1989 | Coulston |
| 6,462,015 B1 | 10/2002 | Weiss |
| 6,524,605 B1 | 2/2003 | Coats |
| 6,673,756 B2 | 1/2004 | Sonnenberg |
| 7,067,677 B2 | 6/2006 | Manzer |
| 7,232,844 B2 | 6/2007 | Hallahan |
| 7,820,145 B2 | 10/2010 | Tamarkin |
| 2003/0062357 A1 | 4/2003 | Schneider et al. |
| 2003/0079786 A1 | 5/2003 | Hallahan |
| 2003/0191047 A1 | 10/2003 | Hallahan |
| 2004/0024054 A1 | 2/2004 | Haenke |
| 2005/0112166 A1 | 5/2005 | Hallahan et al. |
| 2005/0244441 A1 | 11/2005 | Courtois |
| 2006/0148842 A1 | 7/2006 | Scialdone et al. |
| 2006/0223878 A1 | 10/2006 | Scialdone |
| 2006/0240079 A1 | 10/2006 | Hallahan et al. |
| 2007/0077262 A1 | 4/2007 | Scialdone |
| 2007/0264297 A1 | 11/2007 | Scialdone |
| 2008/0305135 A1 | 12/2008 | Kroepke |
| 2010/0034906 A1 | 2/2010 | Gonzalez |
| 2010/0092404 A1 | 4/2010 | Hutchenson |
| 2010/0145077 A1 | 6/2010 | Jackson |
| 2010/0145078 A1 | 6/2010 | Fisher |
| 2010/0168447 A1 | 7/2010 | Hutchenson |
| 2010/0261915 A1 | 10/2010 | Gonzalez |

FOREIGN PATENT DOCUMENTS

WO  WO 03/079786 A1 * 10/2003

OTHER PUBLICATIONS

Phytochemistry, 1967, 6, 1271-1280.*
Regnier et al. 1967, 6, 1281-1288.*
Hutchenson et al., U.S. Appl. No. 60/876,568, filed Dec. 20, 2006.
Jackson et al., U.S. Appl. No. 60/876,569, filed Dec. 21, 2006.
Gonzalez et al., U.S. Appl. No. 60/876,556, filed Dec. 21, 2006.
Scialdone, U.S. Appl. No. 11/266,641, filed Nov. 3, 2005.
Scialdone, U.S. Appl. No. 60/799,277, filed May 9, 2006.
International Search Report, PCT/2007/025984, Dated Jun. 19, 2008.
Regnier et al., Studies on the Composition of the Essential Oils of Three *Nepeta* Species, Phytochemistry, 1967, vol. 6, pp. 1281-1289.
Regnier et al., Nepetalactone and Epinepetalactone From *Nepeta cataria* L., Phytochemistry, 1967, vol. 6, pp. 1271 to 1280.
Perry's Chemical Engineers' Handbook, $7^{th}$ Ed. (1997) Mcgraw-Hill, Section 13.
Tanimori et. al., Total Synthesis of (+) Dihydronepetalactone, Agric. Biol. Chem., 1991, vol. 55:1181-11832.
Fleming et. al., Sterocontrol in Organic Synthesis Using Silicon-Containing Compounds, a Synthesis of (+) Dihydronepetalactone using the Se2 Reaction of an Allysilane, J. Chem. Soc., Perkin Trans, 1998, vol. 1:2645-2649.
Wolinsky et. al., Syntheses of the Dihydronepetalactones, J. Org. Chem., 1972, vol. 37:3376-3378.
Jefson et. al., Chemical Defense of a Rove Bettle, Journal of Chemical Ecology, 1983, vol. 9:150-180.
G.W.K. Cavill et. al., Defensive and Other Secretions of the Australlian Cocktail Ant, Iridomyrmex Nitideceps, Tetrahedron, 1982, vol. 38:1931-1938.
Chris Peterson et. al., Insect Repellents—Past, Present and Future, Pesticide Outlook, Aug. 2001.
Depooter et. al., The Essential Oils Five Nepeta Species. A Preliminary Evaluation of Their Use in Chemotaxonomy by Cluster Analysis, Flavour and Fragrance Journal, 1988, vol. 3:155-159.
Handjieva et. al., Constituents of Essential Oils From Nepeta Cataria L., N. Grandiflora M.B. and N. Nuda L., J. Essential Oil Res., 1996, vol. 8:639-643.
T. Eisner, Science, 1964, vol. 146:1318-1320.

* cited by examiner

*Primary Examiner* — Nizal Chandrakumar

(57) ABSTRACT

Disclosed are methods for treating catmint oil. The treated catmint oil can be used for the production of hydrogenated catmint oil, which is enriched in the insect repellent, dihydronepetalactone, and from which formulated products may be prepared.

10 Claims, No Drawings

SOLVENT ADDITION AND REMOVAL IN THE HYDROGENATION OF CATMINT OIL

This application claims the benefit of U.S. Provisional Application No. 60/876,563, filed 21 Dec. 2006, and U.S. Provisional Application No. 60/876,565, filed 21 Dec. 2006, each of which is incorporated in its entirety as a part hereof for all purposes.

TECHNICAL FIELD

The present invention relates to the hydrogenation of the essential oil of the catmint plant, *Nepeta cateria*. The hydrogenation of the essential oil provides an enriched source of the insect repellent, dihydronepetalactone.

BACKGROUND

Dihydronepetalactone (DHN) has been shown to be an effective insect repellent, as discussed in U.S. Ser. No. 05/112,166. Dihydronepetalactone can be produced by hydrogenating nepetalactone, a component of the essential oil from the catmint plant, *Nepeta cataria* (herein referred to as catmint oil). Catmint oil can be purified from plants of the *N. cataria* by various isolation processes including steam distillation [Regnier, F. E. et al, *Phytochemistry* (1967) 6:1281-1289], organic solvent extraction, microwave-assisted organic solvent extraction, supercritical fluid extraction, mechanical extraction and enfleurage (initial cold extraction into fats followed by organic solvent extraction). The catmint oil so obtained can be used in the crude form to produce DHN, however the hydrogenation reaction can be adversely affected by undesirable components contaminating the crude catmint oil.

Nepetalactone has been purified from catmint oil by crystallization [Regnier, F. E. et al, *Phytochemistry* (1967) 6:1271-1280], however crystallization is expensive, and on the potential scale required for commercialization, it is uneconomical. Therefore, it would be highly desirable to produce a catmint oil with improved properties, such that high yields of the insect repellent DHN may be produced.

SUMMARY

This invention relates to processes for preparing hydrogenated catmint oil, processes for preparing products that are formulated therefrom, the use of such processes, and the products obtained and obtainable by such processes.

In one embodiment of the processes hereof, there is provided a process for preparing hydrogenated catmint oil by (a) distilling crude catmint oil to produce (i) a distillate fraction comprising volatile components driven off from the beginning amount of crude catmint oil, and (ii) a pot fraction; and (b) contacting the pot fraction of step (a) with hydrogen and a hydrogenation catalyst to produce hydrogenated catmint oil.

In another embodiment of the processes hereof, there is provided a process for preparing hydrogenated catmint oil by (a) distilling crude catmint oil to produce (i) a distillate fraction comprising volatile components driven off from the beginning amount of crude catmint oil, and (ii) a pot fraction; and (b) contacting the pot fraction of step (a) with hydrogen and a hydrogenation catalyst to produce hydrogenated catmint oil; wherein one or both of steps (a) and (b) are conducted in the presence of a solvent.

In a further embodiment of the processes hereof, there is provided a process for preparing a product formulated from a hydrogenated catmint oil by (a) distilling a beginning amount of crude catmint oil to produce (i) a distillate fraction comprising volatile components driven off from the beginning amount of crude catmint oil, and (ii) a pot fraction; (b) contacting the pot fraction of step (a) with hydrogen and a hydrogenation catalyst to produce hydrogenated catmint oil; and (c) incorporating the hydrogenated catmint oil produced in step (b) into a formulated product for application to the skin, hide, hair, fur or feathers of a human or a domesticated animal; wherein the distillation of step (a) and/or the hydrogenation of step (b) is conducted in the presence of a solvent.

In yet another embodiment of the processes hereof, there is provided a hydrogenated catmint oil that comprises a 9S dihydronepetalactone.

In yet another embodiment of the processes hereof, a hydrogenated catmint oil may be prepared by (a) distilling a beginning amount of crude catmint oil to produce (i) a distillate fraction comprising volatile components driven off from the crude catmint oil, wherein the weight of the distillate fraction comprises about 2% to about 20% of the weight of the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

In yet another embodiment of the processes hereof, a hydrogenated catmint oil may be prepared by (a) distilling a beginning amount of crude catmint oil that has at least about 150 ppm of sulfur-containing compounds to produce (i) a distillate fraction that comprises at least about 8 wt % of the amount of sulfur-containing compounds in the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

DETAILED DESCRIPTION

This invention relates to processes for preparing hydrogenated catmint oil, processes for preparing products that are formulated therefrom, and the formulated products obtained thereby. Important aspects of this invention therefore relate to methods for treating the essential oil of the catmint plant, *Nepeta cataria*, herein referred to as catmint oil. Methods for treating catmint oil include distillation and/or treatment with an oxidizing agent. The treated catmint oil so produced can be used in a hydrogenation reaction to produce hydrogenated catmint oil, which is enriched in the insect repellent, dihydronepetalactone. DHN in turn may be used for the purpose of preparing a formulated product for application to the skin, hide, hair, fur or feathers of a human or a domesticated animal.

DEFINITIONS

In the description of the processes hereof, the following definitional structure is provided for certain terminology as employed in various locations in the specification:

The structures of 9S dihydronepetalactone stereoisomers are shown below.

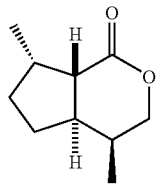
(1S, 5S, 9S, 6R)-5,9-dimethyl-3-oxabicyclo[4.3.0]-nonan-2-one

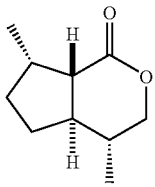
(1S, 9S, 5R, 6R)-5,9-dimethyl-3-oxabicyclo[4.3.0]-nonan-2-one

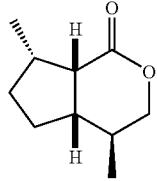
(1S, 5S, 9S, 6S)-5,9-dimethyl-3-oxabicyclo[4.3.0]-nonan-2-one

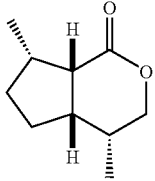
(1S, 9S, 6S, 5R)-5,9-dimethyl-3-oxabicyclo[4.3.0]-nonan-2-one

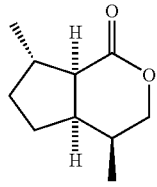
(9S, 5S, 1R, 6R)-5,9-dimethyl-3-oxabicyclo[4.3.0]-nonan-2-one

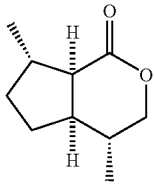
(9S, 1R, 5R, 6R)-5,9-dimethyl-3-oxabicyclo[4.3.0]-nonan-2-one

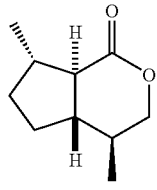
(9S, 6S, 1R, 5S)-5,9-dimethyl-3-oxabicyclo[4.3.0]-nonan-2-one

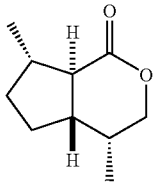
(9S, 6S, 1R, 5R)-5,9-dimethyl-3-oxabicyclo[4.3.0]-nonan-2-one

The term "nepetalactone" as used herein refers to the compound having the general structure of Formula I:

Formula I

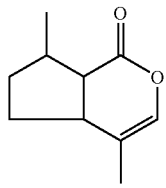

The term "dihydronepetalactone" ("DHN") as used herein refers to the compound having the general structure of Formula II:

Formula II

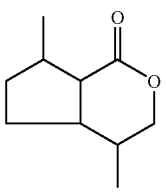

The term "puleganic acid" as used herein refers to the compound having the general structure of Formula III:

Formula III

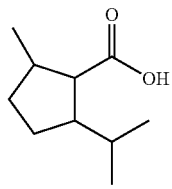

The term "nepetalic acid" as used herein refers to the compound having the general structure of Formula IV:

Formula IV

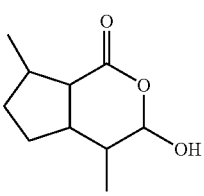

The term "crude catmint oil" as used herein refers to catmint oil that has been obtained from the catmint plant, *N. cataria*, and contains predominantly the trans-cis and/or cis-trans isomers of nepetalactone as shown in Formulae V and VI, respectively.

Formula V

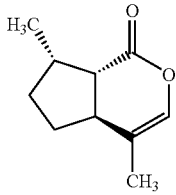

Formula VI

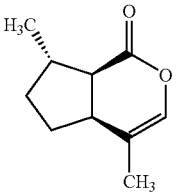

Crude catmint oil may also contain extraneous components such as caryophyllenes, carvones, limonenes and other sesquiterpenes, and other unidentified impurities. One or more of these extraneous components can decrease the effectiveness of the hydrogenation of catmint oil, as measured for example by the rate of conversion of the nepetalactone therein to dihydronepetalactone. The distillation steps of the processes hereof can assist with the removal of one or more of the extraneous components, thereby improving the hydrogenation of catmint oil.

In one embodiment of the processes hereof, there is provided a process for preparing hydrogenated catmint oil by (a) distilling crude catmint oil to produce (i) a distillate fraction comprising volatile components driven off from the beginning amount of crude catmint oil, and (ii) a pot fraction; and (b) contacting the pot fraction of step (a) with hydrogen and a hydrogenation catalyst to produce hydrogenated catmint oil.

In one particular embodiment hereof, a hydrogenated catmint oil may be prepared by (a) distilling a beginning amount of crude catmint oil to produce (i) a distillate fraction comprising volatile components driven off from the crude catmint oil, wherein the weight of the distillate fraction comprises about 2% to about 20% of the weight of the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

In another embodiment the distillate fraction has about 5% to about 10% by weight of the beginning amount of crude catmint oil.

Depending on the process used to obtain catmint oil from *N. cataria*, the extraneous components contained in catmint oil can comprise sulfur-containing compounds, dimethyl sulfide for example, that may decrease the rate of conversion of nepetalactone, possibly by poisoning the hydrogenation catalyst. Sulfur-containing compounds present in the crude catmint oil can be quantitated using X-ray fluorescence spectroscopy.

In another embodiment hereof, a hydrogenated catmint oil may be prepared by (a) distilling a beginning amount of crude catmint oil that has at least about 150 ppm of sulfur-containing compounds to produce (i) a distillate fraction that comprises at least about 8 wt % of the amount of sulfur-containing compounds in the beginning amount of crude catmint oil, and (ii) a pot fraction; (b) contacting the pot fraction produced in step (a) with hydrogen and a hydrogenation catalyst to produce hydrogenated catmint oil; and (c) optionally, recovering the hydrogenated catmint oil of step (b).

In more specific embodiments, the distillate fraction of step (a) comprises at least about 25%, at least about 50% or at least about 75% of the sulfur-containing compounds by weight relative to the beginning amount of sulfur-containing compounds in the crude catmint oil.

Distillation is a well-known process [see, for example, Seader et al, "Distillation", in *Perry's Chemical Engineers' Handbook*, 7$^{th}$ Ed. (1997) McGraw-Hill, Section 13]. Distillation methods suitable for the current process include vacuum distillation, steam distillation and solvent distillation. Both steam and solvent distillation can optionally be performed under vacuum. Distillation of crude catmint oil can be carried out using any suitable apparatus, such as a pot or resin kettle outfitted with a heating element, a shell and tube condenser, and a dry ice finger. The temperature at which distillation and condensation occur will depend on the process used. For example, the heating temperature will be lower when vacuum is applied during the distillation process.

When steam distillation is utilized, approximately 2% to about 40% water (by weight relative to the weight of the catmint oil plus the water) may be added to the catmint oil. In a more specific embodiment, approximately 5% to about 20% water (by weight relative to the weight of the catmint oil plus the water) may be added to the catmint oil. In one embodiment, the mixture of catmint oil and water can be distilled at a temperature of about 100° C., i.e. the boiling point of the water, at atmospheric pressure. In an alternative embodiment, the distillation can be performed at an absolute pressure of less than or equal to about 68.9 kPa. In yet another embodiment, the distillation can be performed at an absolute pressure of less than or equal to about 41.4 kPa. At lower pressures, the distillation temperature will be lower due to the lower boiling point of water at reduced pressure.

Solvent distillation refers to a distillation process whereby a solvent is added to aid in the separation of components of close-boiling mixtures. "Close-boiling" mixtures are mixtures wherein the boiling points of the components are similar. In this invention, the solvent used is typically more volatile than the catmint oil, and when distilled off, removes some of the volatile species present in the crude oil. Preferably the solvent is a compound that is inert to the catmint oil. Solvents suitable for this invention include $C_1$ to $C_5$ straight-chain or branched alcohols. In one embodiment, the solvent is an alcohol selected from the group consisting of methanol, ethanol, isopropanol and n-propanol.

Preferably, the initial solvent concentration is from about 5% to about 60% by weight relative to the combined weight of the catmint oil plus the solvent. In another embodiment, the initial solvent concentration is from about 10% to about 25% by weight relative to the combined weight of the catmint oil plus the solvent. Solvent distillation can be performed at atmospheric pressure. In an alternative embodiment, the distillation is performed at an absolute pressure of less than or equal to about 68.9 kPa. In yet another embodiment, the distillation is performed at an absolute pressure of less than or equal to about 41.4 kPa. The temperature at which solvent distillation is carried out will depend on parameters such as the solvent used, the concentration of the solvent, and the pressure at which the distillation is carried out. Typical temperatures range from about 50° C. to about 100° C.

In a further embodiment of this invention, solvent distillation can be combined with steam distillation. For example, one could carry out steam distillation of crude catmint oil as described above to obtain a catmint oil from which some of the volatile components and most of the water have been removed. In a second distillation step, this steam distilled catmint oil is then contacted with a solvent, and solvent distillation is performed as described above. Solvent distillation will remove additional volatile components not removed by steam distillation. In addition, solvent distillation can be used to remove residual water introduced into the catmint oil during steam distillation.

At temperatures above about 80° C., nepetalactone isomers in wet catmint oil may hydrolyze to undesirable products, such as nepetalic acid. The rate of hydrolysis increases with temperature up to about 200° C., where the catmint oil thermally degrades. Therefore, it would be desirable to be able to carry out the distillation of catmint oil at a lower temperature to avoid the hydrolysis of nepetalactone. The temperature can be reduced by operating the distillation apparatus under vacuum. The amount of vacuum applied to the system will depend on the system components, however achieving a vacuum of less than about 68.9 kPa (absolute) is preferred. In one embodiment, vacuum distillation is performed at an absolute pressure of less than about 6.89 kPa.

In a further embodiment, a step of contacting crude catmint oil with an oxidizing agent can be performed before a step of distillation, as described above, is performed.

Examples of oxidizing agents suitable for use herein to contact with crude catmint oil include $Na_2B_4O_7 \cdot 10H_2O$, which is available for example in a product such as 20 Mule Team® Borax. In one embodiment, contacting can occur by mixing the catmint oil with $Na_2B_4O_7 \cdot 10H_2O$, followed by filtering the mixture to separate the $Na_2B_4O_7 \cdot 10H_2O$ from the oxidized catmint oil. In an alternative embodiment, the $Na_2B_4O_7 \cdot 10H_2O$ can be placed in a column, and the crude catmint oil can be drained through the column. $Na_2B_4O_7 \cdot 10H_2O$ can be used at a concentration of about 1% to about 50% by weight relative to the combined weight of the $Na_2B_4O_7 \cdot 10H_2O$ plus the catmint oil. In more specific embodiments, $Na_2B_4O_7 \cdot 10H_2O$ can be used at concentrations of about 3% to about 50% and about 15% to about 50% by weight relative to the combined weight of the Na$_2$B$_4$O$_7$.10H$_2$O plus the catmint oil.

Other suitable oxidizing agents for use to contact with crude catmint oil include a hydrogen peroxide solution, which can be used at a concentration of about 1% to about 15% relative to the combined weight of the hydrogen peroxide solution plus the catmint oil. A 30% hydrogen peroxide solution has been found suitable. The mixture of hydrogen peroxide and catmint oil are vigorously agitated, and the aqueous hydrogen peroxide phase is allowed to separate from the organic catmint oil phase. The catmint oil phase can be recovered from the aqueous hydrogen peroxide phase by decantation. Contacting of crude catmint oil with Na$_2$B$_4$O$_7$.10H$_2$O or a dilute hydrogen peroxide solution can be performed at room temperature (about 25° C.).

Ozone is yet another alternative oxidizing agent, which can be used by vigorously agitating the crude catmint oil in the presence of ozone.

Examples of the performance of the above described methods of distilling and purifying crude catmint oil are described in U.S. Provisional Application No. 60/876,569, which is incorporated in its entirety as a part hereof for all purposes.

Crude catmint oil can be obtained from a supplier such as George Thacker Sons (Alberta, Canada), or can be obtained from catmint plant material by known methods, such as distillation [Regnier, F. E. et al, *Phytochemistry* (1967) 6:1281-1289]. One particular method for obtaining catmint oil suitable for use herein includes the steps of (a) contacting plant material with steam whereby a volatilized heterogeneous mixture comprising catmint oil and water is formed; (b) condensing the volatilized heterogeneous mixture to form a heterogeneous liquid condensed mixture comprising catmint oil and water; (c) contacting the heterogeneous liquid condensed mixture of step (b) with sufficient salt such that (1) the resulting mixture has a ratio [$(\rho_{catmint\ oil}-\rho_{aqueous\ solution})$ $\mu_{aqueous\ solution}$] of less than or equal to about −0.05, (2) the resulting solubility of the catmint oil in the salt solution decreases by at least about 50%, or (3) a combination of (1) plus (2), thereby causing the heterogeneous liquid condensed mixture to separate into a catmint oil phase and an aqueous salt solution phase; and (d) recovering the catmint oil phase of step (c). This method is more particularly described in U.S. Provisional Application No. 60/876,556, which is incorporated in its entirety as a part hereof for all purposes.

Following distillation, and optional contact with an oxidizing agent, the pot fraction containing catmint oil can be used in a hydrogenation reaction to obtain hydrogenated catmint oil. The hydrogenation reaction may be carried out in the presence of hydrogen at a temperature of about −10° C. to about 200° C. The hydrogen pressure for the reaction is generally from about 0.1 MPa to about 20.7 MPa. The time, temperature, hydrogen pressure and flow rate and feed may be adjusted, according to known principles, to obtain optimal conversion of hydrogenation of catmint oil using a given catalyst. A suitable hydrogenation reaction is that which is described in U.S. Pat. No. 7,067,677 (which is incorporated in its entirety as a part hereof for all purposes). Described therein is the hydrogenation of nepetalactone in the presence of a catalytic metal that is not nickel, platinum or palladium. The process can be carried out at a temperature of about 25° C. to about 250° C. at a hydrogen pressure of about 0.1 MPa to about 20 MPa. Other suitable processes for making a dihydronepetalactone include a process as described in U.S. Provisional Application No. 60/876,568, which is incorporated in its entirety as a part hereof for all purposes. A hydrogenation reaction may be carried out in batch in a single reactor, in sequential batch in a series of reactors, in reaction zones within one or more reactors, or in continuous mode in any of the equipment customarily employed for continuous processes.

In another embodiment of this invention, the processes hereof provide a hydrogenated catmint oil that comprises a 9S dihydronepetalactone.

A particular embodiment of the processes hereof includes a process for preparing hydrogenated catmint oil by (a) distilling crude catmint oil to produce (i) a distillate fraction comprising volatile components driven off from the beginning amount of crude catmint oil, and (ii) a pot fraction; (b) contacting the pot fraction of step (a) with hydrogen and a hydrogenation catalyst to produce hydrogenated catmint oil; wherein one or both of steps (a) and (b) are conducted in the presence of a solvent. Suitable solvents for either or both such purposes include C$_1$ to C$_5$ straight-chain or branched alcohols, such as an alcohol selected from the group consisting of methanol, ethanol, isopropanol and n-propanol.

In the above process, the distillation of step (a), or the hydrogenation of step (b), or both steps may be conducted in the presence of a solvent. Solvent may be added to the pot fraction produced by step (a) before it is hydrogenated in step (b), or solvent may be present in the hydrogenated catmint oil produced in step (b), and the process may further include a step of removing solvent from the hydrogenated catmint oil produced in step (b). When solvent removal occurs, the process may further include a step of recycling removed solvent to the distillation of step (a) and/or the hydrogenation of step (b).

When the hydrogenation of step (b) is conducted in the presence of solvent, it may be conducted in a plurality of steps, reactor zones or reactors, and solvent may be removed between one step, zone or reactor and the next succeeding step, zone or reactor. As noted above, the process may in such case also include a step of recycling removed solvent to the distillation of step (a) and/or the hydrogenation of step (b).

The embodiment of the processes hereof described above may also include a step of incorporating the hydrogenated catmint oil produced in step (b) into a formulated product for application to the skin, hide, hair, fur or feathers of a human or domesticated animal.

Another alternative embodiment of the processes hereof also includes a step of incorporating hydrogenated catmint oil into a formulated product for application to the skin, hide, hair, fur or feathers of a human or domesticated animal; and generally involves the following steps:

(a) distilling a beginning amount of crude catmint oil to produce (i) a distillate fraction comprising volatile components driven off from the beginning amount of crude catmint oil, and (ii) a pot fraction;

(b) contacting the pot fraction of step (a) with hydrogen and a hydrogenation catalyst to produce hydrogenated catmint oil; and (c) incorporating the hydrogenated catmint oil produced in step (b) into a formulated product for application to the skin, hide, hair, fur or feathers of a human or domesticated animal;

wherein the distillation of step (a) and/or the hydrogenation of step (b) is conducted in the presence of a solvent. Solvents suitable for use in this embodiment include those noted above.

This embodiment of the processes may also include a step of incorporating a solvent into the formulated product, which may be done by adding solvent to the distillation that occurs during step (a), adding solvent to the hydrogenation that occurs during step (b), or adding solvent in both such steps.

In this embodiment, incorporation of solvent into the formulated product may include any two of, or all three of, the steps of (i) adding solvent to the distillation that occurs in step (a), (ii) adding solvent to the hydrogenation that occurs during step (b), and (ii) adding solvent to the hydrogenated catmint oil that is obtained as the product of step (b). The same solvent may be used in all steps. For example, the hydrogenation of step (b) may be conducted in a plurality of steps, reactor zones or reactors, and, in such case, the incorporation of solvent into the formulated product comprises a step of adding solvent to the hydrogenation that occurs in some but not all, or in all, of the steps, zones or reactors.

Following the hydrogenation reaction, the hydrogenated catmint oil can be recovered from the reaction mixture by known methods of separation, such as decantation or filtration. Dihydronepetalactone can be recovered from the hydrogenated catmint oil, for example, by column chromatography.

The processes hereof for distilling and hydrogenating catmint oil provide Hydrogenation Reaction Products ("HRP"). As hydrogenated catmint oil in the form of an HRP may be incorporated into a formulated product for application to the skin, hide, hair, fur or feathers of a human or domesticated animal, this invention relates further to compositions comprising HRP, and to the use of HRP and the compositions thereof. The preparations of this invention, which include the HRP compounds described above, and the compositions, formulations and other materials that may be prepared from such compounds according to this invention, and mixtures thereof, may all be used for a multiplicity of purposes. These purposes include, for example, use as an active ingredient in an effective amount for the repellency of various insect or arthropod species, use as a fragrance compound itself or as an ingredient in a perfume composition, or use as a topical treatment for skin.

For example, the preparations hereof may be applied in a topical manner to the skin, hide, hair, fur, feathers or other surface of a mammal, such as a human or domesticated animal, that serves as a host for an insect or arthropod. Living, animate hosts such as these may serve as insect-acceptable food sources for blood-feeding insects and arthropods such as biting flies, chiggers, fleas, mosquitoes, ticks and lice.

The preparations hereof may also be applied to or incorporated into an inanimate host for an insect or arthropod, which includes for example a food source such as growing or harvested plants or crops, or a desirable habitat such as a building or structure, or other types of protective articles such as may be made from fabrics or textiles. Such inanimate hosts may include, for example, towers, silos, bins, hoppers, boxes and bags in which food products such as grain is stored, which may be an attractive habitat or food source for insects such as flour or bean beetles or weevils. A preparation hereof may be used to repel such insects by applying the preparation to a container or article or to any point of access thereto.

The preparations hereof may also be applied to the skin and/or hair of humans to impart a pleasant odor or aroma as a fragrance compound itself, or as an ingredient in a perfume composition; and the preparations hereof may also be used as a topical treatment for skin by application to the skin and/or hair of humans in the form of a body wash, rinse, conditioner, toner, lotion, splash, spray or other type of cosmetic product as applied personally by the user.

A repellent substance drives insects or arthropods away from their preferred hosts, whether animate or inanimate, or renders those hosts unacceptable in some manner. Most repellents are not active poisons, but rather make desirable insect/arthropod hosts, or the conditions associated with those hosts, unattractive or offensive. Typically, a repellent is a preparation that can be topically applied to, on or about a host, or can be incorporated into a host, to deter insects/arthropods from approaching or remaining in the nearby 3-dimensional space in which the host exists. In either case, the effect of the repellent is to cause the insects/arthropds to reject the host, or to cause them to be driven out of and away from the host, which thereby minimizes the frequency of "bites" to an animate host, or minimizes the amount of damage that the insect/arthropod causes to an inanimate host. Repellents may be in the form of gases (olfactory), liquids, or solids (gustatory).

One property that is important to overall repellent effectiveness is surface activity, as many repellents contain both polar and non-polar regions in their structure. A second property is volatility. Repellents form an unusual class of compounds where evaporation of the active ingredient from a surface of, on or near a host makes an important contribution to its effectiveness, as measured by the protection of an animate host from bites or the protection of an inanimate host from damage.

An aspect of the potency of a repellent substance is the extent to which the concentration of the substance in the air space above or around a surface where it has been applied is sufficient to repel an insect or arthropod, particularly a flying insect. A desirable level of concentration of the repellent is obtained in the air space primarily from evaporation, but the rate of evaporation is affected by the rate of any absorption into the surface, and penetration into and through the surface is thus almost always an undesirable mode of loss of repellent from the surface. This consideration applies equally to the loss of a repellant by absorption into the skin or other surface of an animate host as to the loss of a repellant from a surface of an inanimate host made from a synthetic material, where the repellant substance may undesirably react with other chemicals present on that same surface. Loss of concentration of a repellant substance by physical action, such as dilution or absorption, or loss of concentration by chemical action, such as a reaction, is equally undesirable in the case of repellency of an insect/arthropod that crawls, for which concentration directly on a surface is an important factor.

In selecting a substance for use as an insect/arthropod repellent active, the inherent volatility of the substance thus is generally an important consideration. A variety of strategies are available, however, when needed for the purpose of attempting to increase persistence of the active while not decreasing, and preferably increasing, volatility. For example, the active can be formulated with polymers and inert ingredients to increase persistence on a surface to which applied or from which it will be exuded. The presence of inert ingredients in the formulation, however, dilutes the active in the formulation, and the loss of an active from undesirably rapid evaporation must thus be balanced against the risk of simply applying too little active to be effective. Alternatively, the active ingredient may be contained in microcapsules to control the rate of loss from a surface or an article; a precursor molecule, which slowly disintegrates on a surface or in an article, may be used to control the rate of release of the active ingredient; or a synergist may be used to continually stimulate the evaporation of the active from the formulated composition.

The release of an active ingredient that is intended for application to the skin or other surface of an animate host may be accomplished, for example, by sub-micron encapsulation, in which the active ingredient is encapsulated or enveloped in a skin-nourishing protein. The protein may be used, for example, at about a 20 wt % concentration. An application of repellent contains many of these protein capsules that may be suspended in either a water-based lotion, or water for spray application. After contact with skin, the protein capsules begin to break down, releasing the encapsulated active. The process continues as each microscopic capsule is depleted then replaced in succession by a new capsule that contacts the surface and releases its active ingredient. The process may take up to 24 hours for one application. Because a protein adheres very effectively to skin, these formulations are very resistant to perspiration (sweat-off) and dilution by water from other sources.

One of the distinct advantages of the preparations of this invention is that they are all characterized by a relative volatility that makes them suitable for use to obtain a desirably high level of concentration of active ingredient on, above and around a surface of an animate or inanimate host, as described above. One or more of these preparations may be used for such purpose as an active, or an active formulation, in a composition in which the preparation is admixed with a carrier suitable for wet or dry application of the composition to a surface in the form, for example, of a liquid, aerosol, gel, aerogel, foam or powder (such as a sprayable powder or a dusting powder). Suitable carriers include any one of a variety of commercially available organic and inorganic liquid, solid, or semi-solid carriers or carrier formulations usable in formulating a variety of cosmetic products. When formulating a composition for application to the skin or other surface of a human, it is important to select a dermatologically acceptable carrier. A carrier suitable for use herein may include water, alcohol, silicone, petrolatum, lanolin; or may include an organic liquid carrier such as a liquid aliphatic hydrocarbon (e.g. pentane, hexane, heptane, nonane, decane and their analogs) or a liquid aromatic hydrocarbon.

Examples of other useful liquid hydrocarbons include oils produced by the distillation of coal and the distillation of various types and grades of petrochemical stocks, including kerosene oils that are obtained by fractional distillation of petroleum. Suitable petroleum oils include those generally referred to as agricultural spray oils (e.g. the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other suitable carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials. In addition to the above-mentioned liquid hydrocarbons, the carrier can contain conventional emulsifying agents which can be used for causing the active ingredient to be dispersed in, and diluted with, water for end-use application. Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g. tert-butyl sulfinyl dimethyl dithiocarbonate) can be used in conjunction with, or as a component of, the carrier or carriers used in a composition as made according to this invention.

Numerous clays having a layered structure with interstices, and synthetic inorganic materials that resemble such clays in respect of chemical composition, crystallinity and layered morphology, are suitable for use herein as carriers. Suitable clays having a layered structure with interstices include smectite, kaolin, muscovite, vermiculite, phlogopite, xanthophyllite, and chrysotile, and mixtures thereof. Preferred are smectite clays and kaolin clays. Smectite clays include montmorillonite, beidellite, nontronite, saponite, hectorite, sauconite, and others. Kaolin clays include kaolinite, deckite, nacrite, antigorite, and others. Most preferred is montmorillonite. Average particle sizes range from 0.5 to 50 micrometers.

Desirable properties of an insect/arthropod repellant composition, particularly one to be applied to the skin or other surface of an animate host, include low toxicity, resistance to loss by water immersion or sweating, low or no odor or at least a pleasant odor, ease of application, and rapid formation of a dry tack-free surface film. A composition possessing these properties enables treatment of a domesticated animal infested with an insect/arthropod (e.g. dogs infested with fleas, poultry infested with lice, or cattle infested with horn flies or ticks), or a human experiencing unavoidable exposure to an insect/arthropod, by contacting the skin, hide, hair, fur, feathers or other surface with an amount of the composition effective to repel the insect/arthropod from the host.

The application of an effective amount of an repellant composition on a surface subject to attack by an insect/arthropod (such as the skin, hide, hair, fur, or feathers of an animate host, or the stalks, stems, leaves or flowers of a plant or crop) may be accomplished by dispersing the composition into the air, or by dispersing the composition as a liquid mist or incorporated into a powder or dust, and this will permit the composition to fall on the desired surfaces of a host. It may also be desirable to formulate a repellent composition by combining a preparation hereof with a fugitive vehicle for application in the form of a spray. Such a composition may be an aerosol, sprayable liquid or sprayable powder composition adapted to disperse the active ingredient into the atmosphere by means of a compressed gas, or a mechanical pump spray. Likewise, directly spreading a liquid/semi-solid/solid repellent on a host in wet or dry form (as a friable solid, for example) is a useful method of contacting a surface of the host with an effective amount of the repellent.

Further, it may also be desirable to combine a preparation hereof with one or more other compounds known to have insect repellency in a composition to achieve a synergistic effect. Suitable insect repellant compounds combinable for such purpose include nepetalactones, nepetalactams, dihydronepetalactones and derivatives thereof, dihydronepetalactams and derivatives thereof, benzil, benzyl benzoate, 2,3,4,5-bis(butyl-2-ene)tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normalpropyl isocinchomeronate, 2-phenylcyclohexanol, p-methane-3,8-diol, and normal-propyl N,N-diethylsuccinamate.

In addition to one or more of the preparations hereof, an insect/arthropod repellent composition may also include one or more essential oils and/or active ingredients of essential oils. An essential oil includes any type of volatile oil that is obtained from a plant and possesses the odor and other characteristic properties of the plant. Examples of useful essential oils include: almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

The insects and arthropods that may be repelled by the preparations hereof include any member of a large group of invertebrate animals characterized, in the adult state (non-adult insect states include larva and pupa) by division of the body into head, thorax, and abdomen, three pairs of legs, and, often (but not always) two pairs of membranous wings. This definition therefore includes a variety of biting insects (e.g. ants, bees, chiggers, fleas, mosquitoes, ticks, wasps), biting flies [e.g. black flies, green head flies, stable flies, horn flies (haematobia irritans)], wood-boring insects (e.g. termites), noxious insects (e.g. houseflies, cockroaches, lice, roaches, wood lice), and household pests (e.g. flour and bean beetles, dust mites, moths, silverfish, weevils).

In another embodiment, a preparation hereof may be used as a fragrance material or as an active in a fragrance composition, and be applied in a topical manner to human or animal skin or hair to impart a pleasing scent or aroma thereto, as in colognes or perfumes for humans or pets. Alternatively, the pleasing scent or aroma may be obtained by the use of a preparation hereof as an insect/arthropod repellant where the preparation has the dual attributes of simultaneously imparting both repellency as well as the pleasing scent or aroma.

In a further embodiment, the insect/arthropod repellency and/or fragrance of products directed to other fundamental purposes will be improved by the presence therein of a preparation of this invention. Those other products include, for example, a body wash, rinse, lotion, splash, tonic or toner, bath and shower gels, foam products (e.g. shaving foams), makeup, deodorants, shampoo, hair lacquers/hair rinses, personal soap compositions (e.g. hand soaps and bath/shower soaps) or other personal care treatments or palliatives, and cleaning agents such as detergents and solvents, and air fresheners and odor removers. Such products may be fabricated, for example, in the form of a sprayable liquid, an aerosol, a foam, a cream, an ointment, a gel, a paste, a powder or a friable solid. The process of fabricating such a product would thus include admixing a preparation hereof with suitable carriers or other inert ingredients to facilitate delivery in the physical form as described, such as liquid carriers that are readily sprayed; a propellant for an aerosol or a foam; viscous carriers for a cream, an ointment, a gel or a paste; or dry or semi-solid carriers for a powder or a friable solid.

Any of the above described products may also contain other therapeutically or cosmetically active adjuvants or supplemental ingredients as are typical in the personal care industry. Examples of these include fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; adjuvants such as thickeners, buffering agents, chelating agents, preservatives, gelling agents, stabilizers, surfactants, emolients, coloring agents, aloe vera, waxes, and penetration enhancers; and mixtures of any two or more thereof.

Inanimate hosts into which a preparation hereof may be incorporated to produce an insect/arthropod repellent effect, or to impart an improved fragrance, include articles or manufactured goods such as textile and fibrous goods, clothing, sanitary goods, carpeting, linens, outdoor or military equipment such as tents, tarpaulins, backpacks or mosquito netting, candles, paper, paint, ink, wood products such as furniture, plastics and other polymers, and the like.

A preparation hereof may be formulated as or incorporated into a composition for application to an animate host by any of the same methods known in the cosmetics industry, such as dilution, mixing, thickening, emulsifying, bottling and pressurizing. A preparation hereof may be incorporated into an article that serves as an inanimate host by mixing during production or by post-production steps such as spraying or dipping.

A preparation hereof may be admixed in a composition with other components, such as a carrier, in an amount that is effective for usage for a particular purpose, such as an insect/arthropod repellant, fragrance or other skin treatment. The amount of a HRP as described herein, contained in a composition will generally not exceed about 80% by weight based on the weight of the final product, however, greater amounts may be utilized in certain applications, and this amount is not limiting. More preferably, a suitable amount of a HRP will be at least about 0.001% by weight and preferably about 0.01% up to about 50% by weight; and more preferably, from about 0.01% to about 20% weight percent, based on the total weight of the total composition or article. Specific compositions will depend on the intended use.

Other compositions, materials and methods relevant to the use of a HRP are as disclosed in US 2003/062,357; US 2003/079,786; US 2003/191,047; and US 2006/148,842, each of which is incorporated in its entirety as a part hereof for all purposes.

A hydrogenated catmint oil obtainable by one or more of the processes of this invention may be incorporated into a formulated product for application to the skin, hide, hair, fur or feathers of a human or domesticated animal. For such purpose, the formulated product may contain one or more adjuvants or other ingredients as common for use in the cosmetics industry, including those disclosed in U.S. application Ser. No. 11/266,641, and U.S. Provisional Application No. 60/799,277, each of which is incorporated in its entirety as a part hereof for all purposes.

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated to otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

What is claimed is:

1. A process for preparing hydrogenated catmint oil comprising:
   (a) distilling a beginning amount of crude catmint oil to produce (i) a distillate fraction comprising volatile components driven off from the beginning amount of crude catmint oil, and (ii) a pot fraction; and
   (b) contacting the pot fraction of step (a) with hydrogen and a hydrogenation catalyst to produce hydrogenated catmint oil;
   wherein one or both of steps (a) and (b) are conducted in the presence of a solvent;
   wherein the distillation of step (a) comprises a steam distillation followed by a solvent distillation; and
   wherein the beginning amount of crude catmint oil has at least about 150 ppm of sulfur-containing compounds, and the distillate fraction comprises at least about 8 wt % of the amount of sulfur-containing compounds in the beginning amount of crude catmint oil.

2. The process of claim 1 wherein the distillation of step (a) is conducted in the presence of a solvent.

3. The process of claim 1 wherein the hydrogenation of step (b) is conducted in the presence of a solvent.

4. The process of claim 1 wherein the distillation of step (a) and the hydrogenation of step (b) are both conducted in the presence of a solvent.

5. The process of claim 1 wherein solvent is added to the pot fraction produced by step (a) before it is hydrogenated in step (b).

6. The process of claim 1 wherein solvent is present in the hydrogenated catmint oil produced in step (b), and the process further comprises a step of removing solvent from the hydrogenated catmint oil produced in step (b).

7. The process of claim 6 further comprising a step of recycling removed solvent to the distillation of step (a) and/or the hydrogenation of step (b).

8. The process of claim 1 wherein the hydrogenation of step (b) is conducted in the presence of solvent; is conducted in a plurality of steps, reactor zones or reactors; and solvent is removed between one step, zone or reactor and the next succeeding step, zone or reactor.

9. The process of claim 8 further comprising a step of recycling removed solvent to the distillation of step (a) and/or the hydrogenation of step (b).

10. The process of claim 1 wherein steps (a) and (b) are conducted in the presence of the same solvent.

* * * * *